(12) United States Patent
Shworak et al.

(10) Patent No.: US 7,166,763 B2
(45) Date of Patent: Jan. 23, 2007

(54) MOUSE MODEL OF MYXOMATOUS VALVULAR DISEASE

(75) Inventors: Nicholas W. Shworak, Hanover, NH (US); Robert D. Rosenberg, Boston, MA (US); Robert T. Palac, Hanover, NH (US)

(73) Assignees: Trustees of Dartmouth College, Hanover, NH (US); Massachusetts Institute of Technology (MIT), Cambridge, MA (US)

( * ) Notice: Subject to any disclaimer, the term of this patent is extended or adjusted under 35 U.S.C. 154(b) by 0 days.

(21) Appl. No.: 10/365,140

(22) Filed: Feb. 10, 2003

(65) Prior Publication Data

US 2004/0158881 A1    Aug. 12, 2004

(51) Int. Cl.
- *A01K 67/027* (2006.01)
- *A01K 67/00* (2006.01)
- *A01K 67/033* (2006.01)
- *C12N 15/00* (2006.01)

(52) U.S. Cl. .................... 800/18; 800/8; 800/9; 800/22

(58) Field of Classification Search .................... 800/8, 800/18, 4, 21, 3, 22, 25, 9; 435/455, 463, 435/320.1, 325
See application file for complete search history.

(56) References Cited

U.S. PATENT DOCUMENTS

2002/0022255 A1   2/2002   Keith et al. ................. 435/193

FOREIGN PATENT DOCUMENTS

WO    WO 99/22005    6/1999

OTHER PUBLICATIONS

Gardner RL and Brook FA. International J. of Dev. Biol. 41:235-243, 1997.*
Seamark, Reprod. Fertil. Dev. 6: 653-657, 1994.*
Mullins JJ et al. Hypertension 22:630-633, 1993.*
Cameron ER. Molecular Biotechnology 7:253-265, 1997.*
Hammer RE et al. Cell 63:1099-1112. 1990.*
Shworak et al. Glycoconjugate Journal 19:355-361, 2003.*
Polejaeva. Reprod. Supp., 58:293-300 (2001).*
Shworak et al. Glycoconjugate Journal, 19:355-361 (2003).*
SpringerLink Glycoconjugate Journal [online], retrieved Jan. 5, 2006. Retrieved from the Internet:, http://www.springerlink.com/(b5wptgzv3tzgos554u0dlj55)/app/home/contribution.asp?referrer=parent&backto=issue,19,20;journal,21,73;linkingpublicationresults,1:100.*

* cited by examiner

*Primary Examiner*—Ram R. Shukla
*Assistant Examiner*—Thaian N. Ton
(74) *Attorney, Agent, or Firm*—Licata & Tyrrell P.C.

(57) ABSTRACT

An animal selected for lacking heparan sulfate 3-O-sulfotransferase-1 activity is provided. This animal exhibits characteristics associated with myxomatous valvular disease and is useful for identifying agents which prevent, delay or treat myxomatous valvular disease. Methods of diagnosing myxomatous valvular disease are also provided.

4 Claims, 1 Drawing Sheet

SEQUENCE LISTING

<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 1
attggcaact ggagatactc atgt                    24

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
tgccttctcc ggtgtcctct                         20

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 3
ttctgtacag tattagattc acagt                   25

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 4
gctattttgg attggaggca ggt                     23

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 5
ggatccctcg cctggtctta c                       21

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 6
tctagaagtc aaatatacac agagt                   25

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 7
ctcctgagtc acctacactg ag                      22

<210> SEQ ID NO 8
<211> LENGTH: 23
<212> TYPE: DNA
<213> ORGANISM: Artificial Sequence -continued

```
<220> FEATURE:
<223> OTHER INFORMATION: Synthetic oligonucleotide primer

<400> SEQUENCE: 8
ggatccagga ctaactgact ttt                                                23

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 9
ttctgtacag tattagattc acagt                                              25

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 10
gctattttgg attggaggca ggt                                                23

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 11
gccagcgggg ctgctaaa                                                      18

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 12
gcagagatga gttccgctta c                                                  21
```

MOUSE MODEL OF MYXOMATOUS VALVULAR DISEASE

INTRODUCTION

This invention was made in the course of research sponsored by the National Institutes of Health (NIH Grant No. PO1 HL41484-12). The U.S. government may have certain rights in this invention.

BACKGROUND OF THE INVENTION

Hemostatic tone is dynamically established as the net balance between ongoing procoagulant versus anticoagulant and fibrinolytic processes. Antithrombin (AT) is a major anticoagulant that slowly neutralizes proteases of the coagulation cascade through the formation of 1:1 enzyme•AT complexes. The rate of neutralization is dramatically enhanced by heparin, a variant of heparan sulfate (HS) from mast cells. It has been hypothesized that heparan sulfate proteoglycans (HSPGs) on the endothelial cell surface might similarly accelerate AT activity and thereby contribute to the nonthrombogenic properties of blood vessels (Damus, et al. (1973) *Nature* 246:355–357). Indeed, the perfusion of purified thrombin (T) and AT into the hind limbs of rodents led to an elevated rate of T•AT complex formation that was HS-dependent. Endothelial cells produce only a small subpopulation of anticoagulant heparan sulfate ($HS^{act}$) that binds AT and accelerates in vitro T•AT complex generation (Rosenberg, et al. (1997) *J. Clin. Invest.* 99:2062–2070; Rosenberg (2001) *Thromb. Haemost.* 86:41–50). This property distinguishes $HS^{act}$ from the bulk of endothelially generated heparan sulfate ($HS^{inact}$), which lacks in vitro anticoagulant activity. However, it is unclear whether $HS^{act}$ is a major physiologic modulator of hemostasis.

For major hemostatic regulators, changes in the activity level can result in a hypercoagulable state (Rosenberg (2001) supra; Thomas and Roberts (1997) *Ann. Intern. Med.* 126:638–644; Hogan, et al. (2002) *Thromb. Haemost.* 87:563–574). For example, mutations that reduce the level of AT activity primarily predispose patients to venous thrombosis. Complete AT deficiency appears incompatible with human life, and in mice causes intrauterine death from an extreme hypercoagulable state, consumptive coagulopathy (van Boven and Lane (1997) *Semin. Hematol.* 34:188–204; Ishiguro, et al. (2000) *J. Clin. Invest.* 106:873–878). Yet, the contribution of $HS^{act}$ deficiency towards human hypercoagulable states is unknown.

Modulation of $HS^{act}$ levels requires knowledge of $HS^{act}$ structure and biogenesis. HS and heparin are functionally diverse biopolymers that occur on specific core proteins as a repeated disaccharide unit (N-acetylglucosamine α1->4 hexuronic acid β1->4) that is partially decorated with N- and O-sulfate groups. The specific arrangement of these substituents gives rise to distinct binding motifs that activate an array of important biologic effector molecules. Such structures arise through remodeling of the copolymer backbone by a relatively ordered series of reactions involving four families of sulfotransferases (Iozzo (2001) *J. Clin. Invest.* 108:165–167; Esko and Lindahl (2001) *J. Clin. Invest.* 108:169–173). For AT, the minimum binding domain generated in $HS^{act}$ and heparin is the pentasaccharide: ->N-acetylglucosamine 6-O-sulfate->glucuronic acid->glucosamine N-sulfate 3-O-sulfate±6-O-sulfate->iduronic acid 2-O-sulfate->glucosamine N-sulfate 6-O-sulfate->. AT forms specific contacts with several moieties; however, the central 3-O-sulfate group is absolutely essential for both high affinity binding and enhancement of AT activity (Rosenberg, et al. (1997) supra). 3-O-sulfates are the rarest of HS modifications, typically comprising <0.5% of total sulfate moieties (Shworak, et al. (1994) *J. Biol. Chem.* 269:24941–24952; Colliec-Jouault, et al. (1994) *J. Biol. Chem.* 269:24953–24958), suggesting a potential regulatory role.

The regulation of $HS^{act}$ production has been elucidated over the past decade. Core proteins appear to exert minimal influence, as a single core can bear either $HS^{act}$ or $HS^{inact}$ (Shworak, et al. (1994) supra). Instead, $HS^{act}$ results from a discrete biosynthetic pathway regulated by a limiting biosynthetic factor (Shworak, et al. (1994) supra; Colliec-Jouault, et al. (1994) supra). Establishment of conditions for cell-free synthesis of $HS^{act}$ revealed a limiting activity that modifies only a portion of potential precursors, thereby defining cellular production of $HS^{act}$ (Shworak, et al. (1996) *J. Biol. Chem.* 271:27063–27071). The critical enzyme was purified, cloned and identified as the long sought heparan sulfate 3-O-sulfotransferase-1 (also known as heparin-glucosamine 3-O-sulfotransferase, 3-OST-1) (Liu, et al. (1996) *J. Biol. Chem.* 271:27072–27082; Shworak, et al. (1997) *J. Biol. Chem.* 272:28008–28019; WO 99/22005). 3-OST-1 preferentially modifies selected HS structures to create the minimum binding domain pentasaccharide. 3-OST-1 also creates a limited range of 3-O-sulfated structures that do not bind AT (Zhang, et al. (2001) *J. Biol. Chem.* 276:28806–28813), but the biologic relevance of these structures is unknown. To date, 3-OST-1 has only been implicated in regulating hemostatic tone.

Four additional 3-OST isoforms have been isolated, but these isoforms have dramatically distinct substrate preferences; therefore they may regulate distinct biologic properties of HS (Shworak, et al. (1999) *J. Biol. Chem.* 274:5170–5184; Liu, et al. (1999) *J. Biol. Chem.* 274:5185–5192; Shukla, et al. (1999) *Cell* 99:13–22). Some of these isoforms can generate $HS^{act}$, but at about 250-fold lower efficiency than 3-OST-1 (Yabe, et al. (2001) *Biochem. J.* 359:235–241). Thus, 3-OST-1 appears to be the dominant isoform regulating in vivo $HS^{act}$ production. Moreover, selective regulation stems from the enzymatic specificity of 3-OST-1 and the paucity of 3-O-sulfates within HS.

U.S. Patent Application No. 20020022255 provides transgenic mice containing sulfotransferase gene disruptions and methods of screening such animals for identification of drugs, pharmaceuticals, therapies, and interventions which may be effective in treating a disease or other phenotypic characteristics of the animal. Specifically provided are phenol/aryl forms of sulfotransferases which, when deleted in a transgenic animal result in behavioral phenotypes of aggression, hyperactivity, increased activity or decreased anxiety.

It has now been found that mice selected for lacking 3-OST-1 activity exhibit characteristics associated with myxomatous valvular disease.

SUMMARY OF THE INVENTION

One aspect of the present invention is an animal selected for lacking heparan sulfate 3-O-sulfotransferase-1 (3-OST-1) activity. Such an animal exhibits characteristics associated with myxomatous valvular disease and is therefore useful as a model for human myxomatous valvular disease.

Another aspect of the present invention is a method of producing an animal selected for lacking 3-OST-1 activity. The method provides introducing a transgene containing 3-OST-1 nucleic acid sequences and a selectable marker into a first and second isocongenic animal. First and second isocongenic heterozygous animals containing the transgene are then obtained by screening methods. In a preferred embodiment, the first and second isocongenic heterozygous animals are maintained by backcrossing said first and second isocongenic heterozygous animals to respective first and second inbred animals. Homozygous animals selected for lacking 3-OST-1 activity are generated by crossing the first and second isocongenic heterozygous animals.

Another aspect of the present invention is a method of screening for an agent for treatment of myxomatous valvular disease. The method provides administering an agent to an animal selected for lacking 3-OST-1 activity, wherein said animal exhibits characteristics of myxomatous valvular disease, and determining whether the agent at least partially abates at least one of the characteristics of myxomatous valvular disease in said animal.

A further aspect of the present invention is a method of screening for an agent that prevents or delays the development of myxomatous valvular disease. The method provides administering an agent to an animal selected for lacking heparan sulfate 3-O-sulfotransferase-1 activity, wherein said animal is capable of exhibiting characteristics of myxomatous valvular disease and determining whether the agent at least partially prevents or delays the age of development of at least one of the characteristics of myxomatous valvular disease in said animal compared to the age of development of said characteristic in an untreated animal.

A still further aspect of the present invention is a method of diagnosing a myxomatous valvular disease. The method provides detecting the level or mutation of 3-OST-1 in a sample wherein a mutation or decrease in the level of 3-OST-1 is indicative of a myxomatous valvular disease. In a preferred embodiment, the level of 3-OST-1 protein is detected using an antibody which specifically binds 3-OST-1. In this embodiment, the level of 3-OST-1 protein is detected by contacting the sample with the 3-OST-1 specific antibody so that said antibody binds to 3-OST-1; detecting bound antibody; and comparing the level of the 3-OST-1 to a known standard. In another preferred embodiment, the level of 3-OST-1 activity is detected by evaluating the level of 3-OST-1 activity and comparing the 3-OST-1 activity level in the sample with a known standard. In another preferred embodiment, the level of 3-OST-1 activity is detected by evaluating the level of RNA transcript encoding 3-OST-1 protein and comparing the 3-OST-1 RNA transcript level in the sample with a known standard. Also provided is a kit for detecting the presence of 3-OST-1 comprising an antibody which specifically binds 3-OST-1.

A further aspect of the present invention is a method of producing an antibody to heparan sulfate 3-O-sulfotransferase-1 protein. This method involves immunizing an animal selected for lacking 3-OST-1 activity with a 3-OST-1 polypeptide or antigenic fragment thereof, so that an antibody to 3-OST-1 is produced.

DETAILED DESCRIPTION OF THE INVENTION

Figures 1, 2:
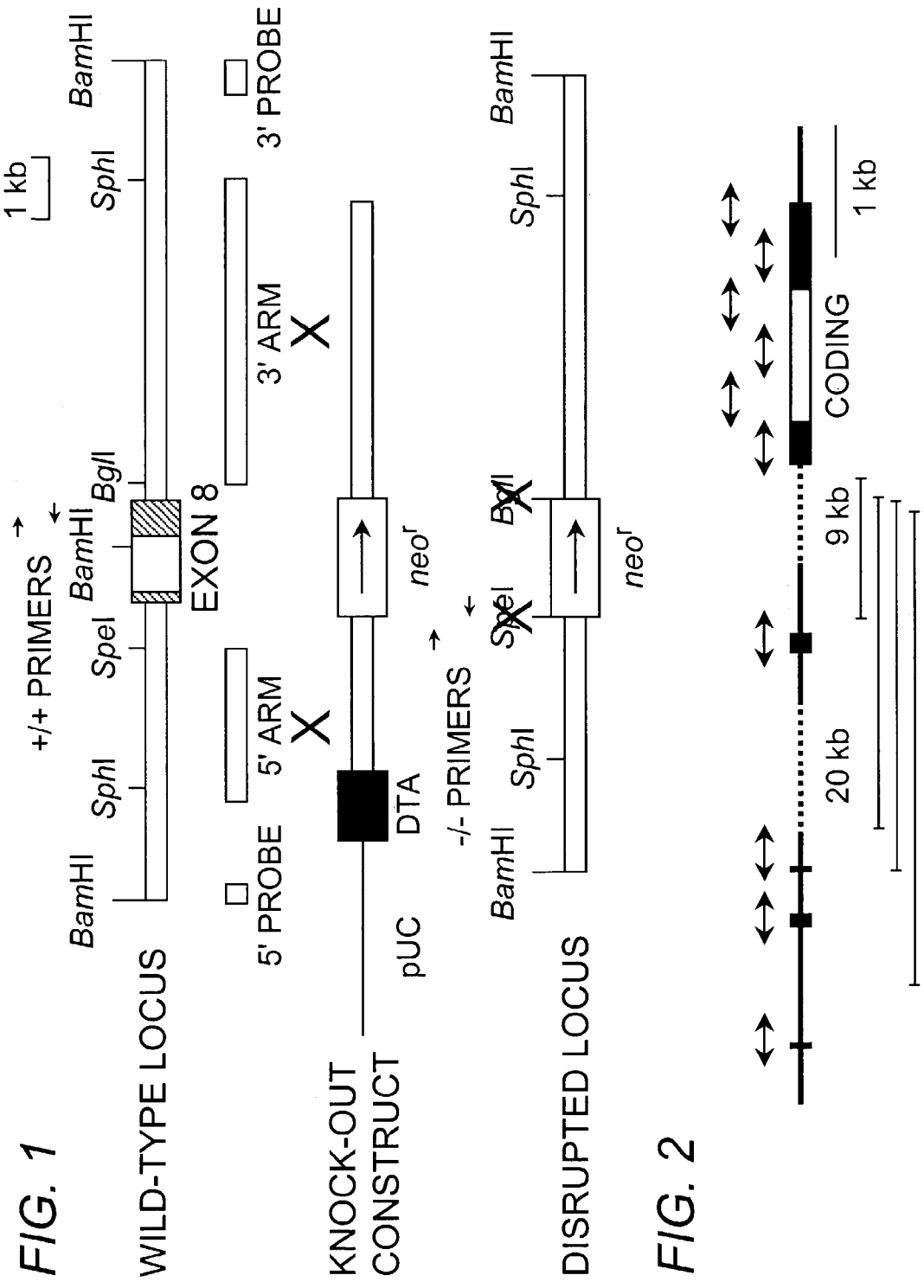
FIG. 1 depicts the strategy for generating animals selected for lacking 3-OST-1 enzyme activity. A portion of the Hs3st1 gene containing exon 8 and 5' and 3' flanking sequences was cloned into a knock-out construct downstream of the selectable marker, diphtheria toxin A (DTA). The neomycin selectable marker (neo$^r$) was inserted into the Hs3st1 gene to replace all of exon 8. A double-crossover event between the knock-out construct and the wild-type Hs3st1 locus results in the replacement of exon 8 with the neo$^r$ marker and hence disruption of the wild-type Hs3st1 gene. Location of probes and primers for analyzing the disrupted locus are indicated.
FIG. 2 depicts the structure of the human HS3ST1 gene. Analysis of human genome databases identified a partial structure for the human HS3ST1. Lower brackets indicate genomic regions removed by variable 5' splicing, based on comparison to EST cDNAs. All identified exons contain polypyrimidine tracts and splice acceptor sites, indicating the promoter region lies further upstream. The last exon contains the entire coding region. Arrows indicate regions for isolation by genomic PCR and sequencing. This region spans ~27 single nucleotide polymorphisms.

Myxomatous valvular disease, also known as mitral valve disease, Barlow disease, chronic valvular disease or endocardiosis, is a common disease that particularly affects the mitral valve. This disease is the most frequent cause of chronic, pure, isolated mitral regurgitation (Schoen (1994) In: Pathologic Basis of Disease, R S Cotran, V Kumar V and S L Robbins (eds) Robbins, 5$^{th}$ ed. Philadelphia, W B Saunders, pp 517–582; Dare, et al. (1993) *Hum. Pathol.* 24:1286). Usually, one or both mitral leaflets are enlarged, redundant or floppy and prolapse, or balloon back into the left atrium, during ventricular systole. Typical histological findings include myxomatous degeneration and degradation of collagen and elastin. The prevalence and severity of the disease increases with age. As a consequence of the progressive valvular degeneration, the valve becomes increasingly insufficient and, in some cases, the degree of mitral regurgitation (MR) becomes so severe that congestive heart failure develops. Once the disease is diagnosed, the valve is typically repaired or replaced as therapeutic agents to delay or prevent valvular degeneration are not available.

Loci linked to myxomatous valvular disease have been mapped to chromosome 16p11.2–p12.1 (Disse, et al. (1999) *Am. J. Hum. Genet.* 65(5):1242–51) and to chromosome Xq28 (Kyndt, et al. (1998) *Am. J. Hum. Genet.* 62(3): 627–32), however, the involved genes have not been identified.

It has now been found that mice selected for lacking 3-OST-1 enzyme activity exhibit many anatomical, histological and functional characteristics observed in human myxomatous valvular disease. Thus, these mice are useful as a model of the human disease and may be used to evaluate therapeutic agents to prevent, delay or treat myxomatous valvular disease. Furthermore, detection of the levels of activity or expression of 3-OST-1 is useful for early diagnosis of myxomatous valvular disease.

The genomic locus of the mouse Hs3st1 is provided in accession number AC118467.20 (exon 1 to intron 4, nucleotides 365061–397744) and accession number AC099813 (intron 4 to exon 8, nucleotides 1–111994). The sequences from these two accession numbers overlap by approximately 2 kb and, without the promoter sequence, the Hs3st1 locus is 141,327 bp. Characterization of the mouse Hs3st1 gene revealed that the entire 3-OST-1 coding region (GENBANK accession number AF019385) was encompassed within exon 8. To generate mice lacking 3-OST-1 enzyme, embryonic stem (ES) cells were electroporated with a replacement vector that eliminated exon 8 (FIG. 1). Southern analyses of 534 G418-resistant ES cell clones with a 3' probe revealed two homologous recombinants. Verification with a 5' probe however, demonstrated only a single clone had undergone appropriate 5' recombination. Only this clone was devoid of exon 8, as revealed by a coding region probe. Further probing for the neomycin resistance gene showed that this clone was devoid of extraneous integrations. Injection of this clone into blastocysts generated chimeric mice that were germ line-competent. Chimeras were bred to C57BL/6J females and interbreeding of heterozygotes resulted in viable mice with comparable recovery of nulls and the wild-types. Tissue homogenates and plasma were evaluated for 3-OST-1 activity by the $HS^{act}$ conversion assay, which measures formation of AT-binding sites within HS. Consistent with the removal of the entire coding region, enzymatic activity was virtually absent in all samples from $Hs3st1^{-/-}$ mice.

3-OST-1 is the predominate source of $HS^{act}$. The effect of Hs3st1 disruption on in vivo levels of $HS^{act}$ was revealed by isolating HS from a variety of tissues. For each tissue examined, recovery of total HS was comparable between $Hs3st1^{-/-}$ and $Hs3st1^{+/+}$ mice. Given the scarcity of 3-O-sulfates within HS (Shworak, et al. (1994) supra; Colliec-Jouault, et al. (1994) supra), altered HS levels should not occur. For most $Hs3st1^{-/-}$ tissues examined, the in vitro anti-Xa activity of HS was reduced by 75–98%, as compared to $Hs3st1^{+/+}$ material. Probing blots of immobilized tissue extracts with $^{125}$I-AT revealed AT-binding sites in $Hs3st1^{-/-}$ mice were similarly reduced. The extent of reduction closely correlated with tissue expression levels of 3-OST-1 mRNA (Shworak, et al. (1999) supra). The minor residual AT-binding sites and anti-Xa activity indicates other 3-OST isoforms can contribute to $HS^{act}$ production. However, for most tissues 3-OST-1 is clearly the predominant isoform and produces the vast majority of AT-binding sites.

Large reductions of $HS^{act}$ might modestly perturb plasma AT levels, given that 10–20% of total body AT is sequestered by vascular endothelial $HS^{act}$ (Carlson, et al. (1984) *J. Clin. Invest.* 74:191–199). Removal of this compartment could produce a slight elevation in plasma AT. Consistent with a loss of vascular $HS^{act}$, baseline plasma AT activity was marginally elevated, by ~15% ($Hs3st1^{+/+}$ 1.8±0.05 U/ml, n=12 versus $Hs3st1^{-/-}$ 2.0±0.12 U/ml, n=7; P<0.05).

$Hs3st1^{-/-}$ mice did not show an obvious procoagulant phenotype. To analyze coagulation, the basal accumulation of fibrin within tissues, an extremely sensitive index of microvascular hemostatic balance (Christie, et al. (1999) *J. Clin. Invest.* 104:533–539; Weiler-Guettler, et al. (1998) *J. Clin. Invest.* 101:1983–1991), was measured. Given the large reductions in $HS^{act}$, it was surprising that tissue fibrin levels for $Hs3st1^{-/-}$ mice were indistinguishable from $Hs3st1^{+/+}$ littermates. Wild-type fibrin accumulation even occurred in organs with extremely low residual levels of anti-Xa activity (e.g., $Hs3st1^{-/-}$ lung and kidney, which had reductions of ~98%). Thus, a basal procoagulant state was not detected.

To uncover a latent procoagulant condition, mice were subjected to a procoagulant challenge, overnight hypoxia (8% $O_2$). Prolonged hypoxia elevates expression of tissue factor in the monocyte/macrophage lineage and in pulmonary vascular endothelial cells, which leads to enhanced fibrin accumulation and pulmonary thrombosis (Weiler-Guettler, et al. (1998) supra; Lawson, et al. (1997) *J. Clin. Invest.* 99:1729–1738). Despite the large $HS^{act}$ reduction in $Hs3st1^{-/-}$ lung, hypoxia-induced fibrin accumulation was comparably elevated (~2.5-fold) in lungs of control and 3-OST-1 deficient animals ($Hs3st1^{+/+}$ 38.4±4.0 μg/g tissue versus $Hs3st1^{-/-}$ 40.1±4.4 μg/g tissue; n=10 littermates per group). Thus, a thrombotic challenge also failed to reveal a microvascular procoagulant state in $Hs3st1^{-/-}$ mice.

Analysis of the macrovasculature, where large accumulations of $HS^{act}$ occur in the subendothelial matrix (de Agostini, et al. (1990) *J. Cell Biol.* 111:1293–1304; Xu and Slayter (1994) *J. Histochem. Cytochem.* 42:1365–1376), was also conducted. To confirm that 3-OST-1 deficiency affects macrovascular $HS^{act}$, AT-binding sites were identified by probing carotid artery cryosections with $^{125}$I-AT. Endothelial $HS^{act}$ was abundant in $Hs3st1^{+/+}$ mice, but was almost undetectable in $Hs3st1^{-/-}$ littermates. The loss of $HS^{act}$ may make $Hs3st1^{-/-}$ vessels prone to rapid thrombosis when the subendothelial matrix is exposed by endothelial injury. This was tested by injuring common carotid arteries with a standardized adventitial application of 30% $FeCl_3$, which results in focal endothelial denudation and rapid development of an occlusive platelet-rich thrombus. This approach is a proven means of documenting accelerated arterial thrombosis (Weiler, et al. (2001) supra; Konstantinides, et al. (2001) *J. Clin. Invest.* 108:1533–1540; Ni, et al. (2001) *Blood* 98:368–373). Moreover, a comparable method has shown the anticoagulant activity of plasma heparan cofactor II (HCII) is only manifest upon exposure of the subendothelial matrix (He, et al. (2002) *J. Clin. Invest.* 109:213–219). It was empirically determined that 30% $FeCl_3$ was the minimum dose required to initiate occlusive thrombosis to allow detection of enhanced thrombosis. Thrombi that formed in wild-type and knock-out mice were comparable by gross histologic inspection. Monitoring blood flow revealed that the time to generate a complete occlusion was indistinguishable between genotypes (P>0.5). A potential difference might be masked if lack of 3-O-sulfates enhances the HCII activity of HS. However, this was ruled out because the HCII activity of tissue HS was identical between genotypes. Immediately after occlusion of both common carotid arteries, an intraventricular blood sample was drawn to measure T•AT complexes. The post injury concentration of T•AT complexes within plasma was independent of mouse genotype (9.1±1.2 μg/L versus 9.7±1.0 μg/L for $Hs3st1^{+/+}$ and $Hs3st1^{-/-}$, respectively). Thus, the profound reduction in subendothelial matrix $HS^{act}$ did not expedite occlusive thrombosis in $Hs3st1^{-/-}$ mice and did not alter post injury levels of T•AT complexes in plasma.

$Hs3st1^{-/-}$ mice have genetic background-dependent, postnatal lethality. $Hs3st1^{-/-}$ mice further developed several unanticipated abnormalities including postnatal lethality and intrauterine growth retardation. Such phenotypes can arise from a gross coagulopathy (Ishiguro, et al. (2000) *J. Clin. Invest.* 106:873–878; Segel and Francis (2000) *Blood Cells Mol. Dis.* 26:540–560). Consequently, it was examined whether perinatal traits of $Hs3st1^{-/-}$ mice stem from such a cause. These phenotypes were detected while altering strain genetic background. Knock-out mice were initially generated on a mixed genetic background (C57BL/6×129S4/SvJae). The knock-out allele was successively bred through C57BL/6 mice. After 7 backcrosses, less than ~1% of the genome is derived from the original ES cell clone; thus, perinatal phenotypes are unlikely to have resulted from a secondary gene mutation. However, targeting of the Hs3st1 locus may have perturbed the expression of adjacent genes thus causing the phenotype.

To determine the involvement of a gross procoagulant state in these phenotypes, $Hs3st1^{+/-}$ mice, from various backcrosses, were interbred to produce litters on progressively enriched C57BL/6 backgrounds. Surprisingly, the recovery of $Hs3st1^{-/-}$ weanlings dramatically diminished as C57BL/6 content increased (a representative lineage presented in Table 1).

TABLE 1

| Parental Background[A] | Offspring C57BL/6 Content | Offspring Hststl genotype | | |
|---|---|---|---|---|
| | | +/+ | +/− | −/− |
| N1 | ~50.0% | 35 | 106 | 35 |
| N3 | ~87.5% | 21 | 45 | 5 |
| N4 | ~93.8% | 16 | 13 | 1 |
| N6 | ~98.4% | 10 | 17 | 12 |
| N6 | ~98.4% | 18 | 26 | 11 |
| N7 (ET) | ~99.2% | 14 | 8 | 2 |
| N8$_{male}$ X 129S4/SVJae$_{female}$ | 50.0% | 25 | 56 | 22 |

| Parental Background[A] | +/+:−/− ratio | Loss of Hs3st1$^{−/−\,B}$ | p[C] | Age[D] |
|---|---|---|---|---|
| N1 | 1:1 | — | | P21 |
| N3 | 1:0.24 | 76% | <0.003 | P21 |
| N4 | 1:0.06 | 94% | <0.001 | P21 |
| N6 | 1:1 | — | | E18.5 |
| N6 | ~1:1 | 39% | | P0 + P1 |
| N7 (ET) | 1:0.14 | 86% | <0.001 | P14 |
| N8$_{male}$ X 129S4/SVJae$_{female}$ | 1:1 | — | | P21 |

[A]N indicates number of successive backcrosses to generate parental Hstst1$^{+/−}$. ET indicates litters were generated by embryo transfer into FVB/N females.
[B]Loss expressed relative to Hstst1$^{+/+}$.
[C]Probability of a non-Mendelian outcome determined by Chi-squared test.
[D]Age at which tissue was collected for genotyping. P indicates days post birth whereas E indicates embryonic days post conception.

After 4 backcrosses, recovery of Hs3st1$^{−/−}$ weanlings bottomed out at ~10% of Hs3st1$^{+/+}$ levels (Table 1, compare N4 to N7). Hs3st1$^{+/−}$ mice showed a partial effect with recovery being ~35% of expected (N4+N7 litters had 30 Hs3st1$^{+/+}$ and should have produced 60 Hs3st1$^{+/−}$). Hs3st1$^{−/−}$ lethality persisted even when litters were produced by embryo transfer into the high fecundity mouse strain FVB/N (Table 1, N7 (ET)). Thus, lethality was predominantly dependent on offspring genotype rather than maternal genotype. The requirement for an enriched C57BL/6 background was further confirmed by breeding Hs3st1$^{+/−}$ mice from the 8$^{th}$ generation backcross (N8) to Hs3st1$^{+/−}$ mice produced on an incipient congenic 129S4/SvJae background. Hs3st1$^{−/−}$ lethality was completely rescued by the resulting hybrid background.

Antithrombin deficient (ATIII$^{−/−}$) mice had intrauterine lethality with no survival past E16.5 (Ishiguro, et al. (2000) J. Clin. Invest. 106:873–878). Given that a gross hypercoagulable state is causative, it was examined if Hs3st1$^{−/−}$ lethality mimics AT deficiency. However, Hs3st1$^{−/−}$ mice showed normal viability one day before birth (E18.5) with only slight reductions within 48 hours of delivery (Table 1, genotype analysis of P0/P1 at N6). The lethality is likely complete by P2–P3 as reductions in litter size were frequently observed during this period. Thus, in contrast to ATIII$^{−/−}$ mice, Hs3st1$^{−/−}$ mice exhibited postnatal rather than intrauterine lethality. In humans, AT deficiency and other hypercoagulable states can lead to postnatal lethality from purpura fulminans (van Boven and Lane (1997) supra); however, bruising and subcutaneous hemorrhages were not evident in newborn Hs3st1$^{−/−}$ pups, despite being subjected to normal birth trauma. Furthermore, Hs3st1$^{−/−}$ newborns had unlabored breathing, ingested milk, produced and excreted urine, and exhibited normal startle reflexes to noise and motion. Thus, a gross cause for postnatal lethality was not readily apparent. Histological surveys of E18.5 and P0 mice failed to reveal thrombosis, hemorrhage nor anatomical anomalies in Hs3st1$^{−/−}$ embryos. Most importantly, myocardial and hepatic tissues lacked focal thrombosis and degeneration, which invariably occurs in late stage ATIII$^{−/−}$ embryos (Ishiguro, et al. (2000) J. Clin. Invest. 106:873–878). Thus, Hs3st1$^{−/−}$ lethality is distinct from ATIII$^{−/−}$ lethality.

It was found that Hs3st1$^{−/−}$ embryos showed intrauterine growth retardation. Although anatomical malformations were not apparent, Hs3st1 genotype did influence embryonic mass in a dose-dependent fashion. Compared to wild-type embryos, Hs3st1$^{+/−}$ and Hs3st1$^{−/−}$ E18.5 embryos were 8% and 20% underweight, respectively, and thus exhibited intrauterine growth retardation (IUGR). Although suckling reduces weight differences, growth retardation remained detectable in newborns (at P0 Hs3st1$^{+/+}$ $^{were}$ 1.26±0.02 gram, n=12, verses 1.14±0.04 gram for Hs3st1$^{−/−}$, n=7; P<0.01). Procoagulant states have been proposed to induce placental vascular insufficiency and thereby cause IUGR (Peeters (2001) Eur. J. Obstet. Gynecol. Reprod. Biol. 95:202–205). However, embryo/placental-disk ratios, which are typically elevated in placental insufficiency, were comparable between genotypes (Hs3st1$^{+/+}$ and Hs3st1$^{−/−}$ values were, 19.7±0.8 versus 20.8±1.1, respectively). IUGR from placental insufficiency also usually shows sparing of head growth (asymmetric IUGR) (Lang, et al. (2000) Am. J. Physiol. Regul. Integr. Comp. Physiol. 279:R53–59; Lin and Santolaya-Forgas (1998) Obstet. Gynecol. 92:1044–1055). Yet, Hs3st1$^{−/−}$ embryos, compared to Hs3st1$^{+/+}$ gestation mates, showed a significant reduction in the biparietal diameter; an established parameter of embryonic head growth (Dilmen, et al. (1996) Fetal Diagn. Ther. 11:50–56). To assess whether reductions in head growth and embryonic mass were proportionate, a modified ponderal index (embryo mass÷(biparietal diameter)$^3$) was calculated. This index was indistinguishable between genotypes (Hs3st1$^{+/+}$, Hs3st1$^{+/−}$ and Hs3st1$^{−/−}$ values were 3.9±0.20, 4.0±0.19 and 4.1±0.18 g/mm$^3$, respectively) indicating that Hs3st1$^{−/−}$ mice exhibit symmetric IUGR. Thus, the IUGR of Hs3st1$^{−/−}$ embryos was not indicative of placental vascular insufficiency. In a mouse model of thrombotic placental insufficiency that produces a comparable degree of IUGR (E18 embryos being 20% underweight), placentae exhibit fibrin thrombi and congestion (Sugimura, et al. (1999) Placenta 20:555–560). However, Hs3st1$^{−/−}$ placentae were microscopically normal. Nor was there evidence of giant cell hyperplasia, a feature of severe placental ischemia. Combined the data indicate the IUGR of Hs3st1$^{−/−}$ mice did not stem from an overt procoagulant state.

Analysis of young Hs3st1$^{−/−}$ mice (i.e., up to 21 days of age) indicated that a large reduction in HS$^{act}$ did not affect hemostatic tone. Thus, normal levels of HS$^{act}$ are not essential for normal hemostasis. To further evaluate the phenotypes associated with the Hs3st1$^{−/−}$ genotype, Hs3st1$^{−/−}$ mice were allowed to mature and were observed over time. An initial histologic evaluation was conducted on step sections of hearts from mice with a mixed genetic background. Hs3st1$^{−/−}$ (n=23) compared to a pool of Hs3st1$^{+/−}$ and Hs3st1$^{+/+}$ (n=15) showed a 4-fold increased frequency of myxomatous valvular disease in aortic leaflets (P<0.02) and a trend towards mitral involvement (2-fold, P<0.3). Involved leaflets showed focal thickening with degradation of fibrosa collagen fibers, increased interstitial cells, accumulation of hyaluronan rich myxoid material, and occasional adherent platelet thrombi. Subsequent evaluations used animals of a pure genetic background to eliminate potential influences of modifier genes.

Analysis of echocardiograph data from older human patients with myxomatous valvular disease indicated that there is also frequent involvement of the aortic valve (Table 2).

TABLE 2

| | N | Prevalence of Total | Prevalence of MVP | Age (±S.D.) |
|---|---|---|---|---|
| Total Patients | 3512 | 100% | — | 64 (±16) |
| All MVP | 84 | 2.4% | 100% | 67 (±16) |
| All AVab | 57 | 1.6% | — | 71 (±13) |
| MVP Alone | 45 | 1.3% | 53.6% | 62 (±17) |
| AV Alone | 18 | 0.51% | — | 66 (±11) |
| MVP + AVab | 39 | 1.1% | 46.4% | 72 (±13) |

MVP, mitral valve prolapse; AVab, aortic valve abnormalities.

Echocardiography was conducted on 20 mice aged from 45 to 80 weeks. Similar to humans, $Hs3st1^{-/-}$, compared to $Hs3st1^{+/+}$, showed enhanced leaflet thickening in both aortic ($P<0.008$) and mitral valves ($P<0.05$), as revealed by M-mode analysis. Aortic valve thickening likely reduced leaflet compliance as valvular resistance (determined by Pulsed wave Doppler) was elevated in $Hs3st1^{-/-}$ mice ($P<0.05$). In ~20% of $Hs3st1^{-/-}$, large platelet thrombi were grossly evident on mitral leaflets ($P<0.06$ compared to $Hs3st1^{+/+}$). A summary of the characteristics of myxomatous valvular disease and the presence of these characteristics in $Hs3st1^{-/-}$ mice is provided in Table 3.

TABLE 3

| Common Characteristic | Presence in $Hs3st1^{-/-}$ mice | Presence in humans with MVD |
|---|---|---|
| Genetic Basis | X | X |
| Anatomical | | |
| Degenerative (begins normal but progresses over time | X | X |
| Focal thickening makes redundant gelatinous valve leaflet | X | X |
| Frequent involvement of both mitral and aortic valves | X | X |
| Low body weight | X | X |
| Histological | | |
| Focal thickening | X | X |
| Degradation of fibrosa collagen fibers | X | X |
| Increased interstitial cells | X | X |
| Accumulation of hyaluronan rich myxoid material | X | X |
| Platelet thrombi on leaflets | X | X |
| Left atrial thrombosis | P | X |
| Progresses to focal calcification and scerosis | X | X |
| Functional | | |
| Thickening reduces valve compliance | X | X |
| Valvular insufficiency | P | X |
| Cardiac arrhythmias | P | X |
| Endocarditis | ND | X |
| Embolic ischemia | ND | X |
| Sudden Death | ND | X |

P indicates that statistical significance not achieved.
ND indicates not determined.

The results provided herein show that $Hs3st1^{-/-}$ mice exhibit many anatomical, histological and functional characteristics of authentic human myxomatous valvular disease and indicate that 3-OST-1 deficiency is involved in myxomatous valvular disease in humans. Therefore, an animal selected for lacking 3-OST-1 activity is a model for human myxomatous valvular disease. Mice are often used for animal models because they are easy to house, relatively inexpensive, and easy to breed. However, other animals may also be made in accordance with the present invention such as, but not limited to, monkeys, bovine, sheep, rabbits, dogs and rats.

There are several ways in which to create an animal model for myxomatous valvular disease; preferably, mutagenesis of gametes or genetic engineering.

To inactivate the Hs3st1 gene via x-ray or chemical agents, mutagenesis of gametes followed by fertilization may be employed. Heterozygous offspring may be identified by Southern blot analysis to demonstrate loss of one allele by dosage, or failure to inherit one parental allele using RFLP markers. Alternatively, viable heterozygotes may be identified by PCR sequencing or by a reduction in 3-OST-1 enzyme activity, as determined by measuring plasma 3-OST-1 levels, or a reduction in gene expression as determined by, for example, real-time PCR.

To create a transgenic animal in which 3-OST-1 activity or expression is decreased, it is desirable to inactivate, replace or knock-out the endogenous Hs3st1 gene by homologous recombination of a transgene using embryonic stem cells. A transgene is meant to refer to heterologous nucleic acid that upon insertion within or adjacent to the Hs3st1 gene results in a decrease or inactivation of Hs3st1 gene expression or 3-OST-1 enzyme activity.

A knock-out of the Hs3st1 gene means an alteration in Hs3st1 nucleic acid sequences that results in a decrease of function of the Hs3st1 gene, preferably such that Hs3st1 gene expression or 3-OST-1 enzyme activity is undetectable or insignificant. Knock-outs as used herein also include conditional knock-outs, where alteration of Hs3st1 nucleic acid sequences can occur upon, for example, exposure of the animal to a substance that promotes Hs3st1 gene alteration, introduction of an enzyme that promotes recombination at the Hs3st1 gene site (e.g., Cre in the Cre-lox system), or other method for directing the Hs3st1 gene alteration post-natally. Transgenic animals may be prepared using methods known to those of skill in the art. See, for example, Hogan, et al. (1986) Manipulating the Mouse Embryo: A Laboratory Manual, Cold Spring Harbor Laboratory Press, Cold Spring Harbor, N.Y.

A knock-out construct is a nucleic acid sequence, such as a DNA construct, which, when introduced into a cell, results in suppression (partial or complete) of expression of a polypeptide or protein encoded by endogenous DNA in the cell. An exemplary knock-out construct is provided herein. This construct contains the marker for diphtheria toxin A (DT-A), a first SphI-SpeI fragment from the 5' end of the murine Hs3st1 gene, a second BglII-SphI fragment from the 3' end of the murine Hs3st1 gene and a DNA fragment encoding the neomycin selectable marker positioned between the first and second Hs3st1 fragments. It should be understood by the skilled artisan that any suitable Hs3st1 nucleic acid sequences may be used in the knock-out construct so long as the expression of the endogenous Hs3st1 gene is partially or completely suppressed by insertion of the transgene. Said Hs3st1 nucleic acid sequences may be coding or non-coding sequences of the Hs3st1 gene. In addition to DT-A, thymidine kinase may also be used to increase the frequency of obtaining correctly targeted cells. Suitable selectable markers include, but are not limited to, neomycin, puromycin and hygromycin. Suitable vectors include, but are not limited to, pBLUESCRIPT, pBR322, and pGEM7. Details for preparing the constructs for Hs3st1 null mutations are provided herein.

Embryonic stem (ES) cells are typically selected for their ability to integrate into and become part of the germ line of a developing embryo so as to create germ line transmission of the transgene. Thus, any ES cell line that can do so is suitable for use herein. For example, the D3 ES cell line described herein may be used. Alternatively, suitable cell lines which may be used include, but are not limited to, the 129J ES cell line or the J1 ES cell line. The cells are cultured and prepared for DNA insertion using methods well-known to the skilled artisan (e.g., see Robertson (1987) In: Teratocarcinomas and Embryonic Stem Cells: A Practical Approach, E. J. Robertson, ed. IRL Press, Washington, D.C.; Bradley, et al. (1986) Curr. Topics Develop. Biol. 20:357–371; Hogan, et al. (1986) Manipulating the Mouse Embryo: A Laboratory Manual, Cold Spring Harbor Laboratory Press, Cold Spring Harbor, N.Y.).

Introduction of the knock-out construct into a first ES cells may be accomplished using a variety of methods well-known in the art, including, for example, electroporation, microinjection, and calcium phosphate treatment. For introduction of the DNA sequence, the knock-out construct DNA is added to the ES cells under appropriate conditions for the insertion method chosen. If the cells are to be electroporated, the ES cells and construct DNA are exposed to an electric pulse using an electroporation machine (electroporator) and following the manufacturer's guidelines for use. After electroporation, the cells are allowed to recover under suitable incubation conditions. The cells are then screened for the presence of the knockout construct. In a preferred embodiment, the transgene is introduced into an ES cell line of a second genetic background to facilitate the generation of a second isocongenic heterozygotic mouse line. Alternatively, the second isocongenic heterozygotic line may be derived from a single ES cell mouse lineage by extensive backcrossing, as described herein.

Each knock-out construct DNA to be introduced into the cell is first typically linearized if the transgene has been inserted into a vector. Linearization is accomplished by digesting the knock-out construct DNA with a suitable restriction endonuclease selected to cut only within the vector sequence and not within the transgene sequence.

Screening for cells which contain the transgene (homologous recombinants) may be done using a variety of methods. For example, as described herein, cells can be processed as needed to render DNA in them available for hybridization with a nucleic acid probe designed to hybridize only to cells containing the transgene. For example, cellular DNA can be probed with $^{32}$P-labelled DNA which locates outside the targeting fragment. This technique can be used to identify those cells with proper integration of the transgene. The DNA can be extracted from the cells using standard methods (e.g., see, Sambrook, et al. (1989) Molecular Cloning: A Laboratory Manual, Second Edition, Cold Spring Harbor Laboratory Press, Cold Spring Harbor, N.Y.). The DNA may then be analyzed by Southern blot with a probe or probes designed to hybridize in a specific pattern to genomic DNA digested with one or more particular restriction enzymes.

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3–4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2–3 days pseudopregnant females are appropriate.

Successful incorporation of ES cells into implanted embryos results in offspring termed chimeras. Chimeras capable of germline transmission of the mutant allele are identified by standard methods. Chimeras are bred and the resulting progeny are screened for the presence of the desired alteration (e.g., Hs3st1 knock-out, heterologous human Hs3st1 mutant). This may be done, for example, on the basis of coat color or by obtaining DNA from offspring (e.g., tail DNA) to assess for the transgene, using known methods (e.g., Southern analysis, dot blot analysis, PCR analysis). See, for example, Sambrook, et al. (1989) Molecular Cloning: A Laboratory Manual, Second Edition, Cold Spring Harbor Laboratory Press, Cold Spring Harbor, N.Y.). Transgene expression may also be assessed (e.g., to determine if a replacement construct is expressed) by known methods, such as northern analysis or PCR analysis. If chimeras are bred to mice whose genetic background is equivalent to the employed ES cell line then the resultant progeny that harbor the desired alteration are deemed isocongenic. If chimeras are bred to mice whose genetic background is distinct from the employed ES cell line then the resultant progeny are deemed as hybrids. Isocongenics may also be generated from any genetic background (hybrids, isocongenics of a distinct background, etc.) through backcrossing, i.e., successive iterations of breeding progeny harbouring the mutant allele to a defined inbred mouse stain. For example, 4–5 backcrosses may be required to generate a near incipient isocongenic, 6–9 backcrosses to generate an incipient isocongenic and 10 or greater backcrosses to create an isocongenic strain. Heterozygotic offspring may be interbred to produce homozygous knock-out animals. As described herein, homozygosity for the Hs3st1 gene knock-out has diminished recovery if maintained on an inbred or near inbred genetic background (produced by interbreeding isocongenics, incipient isocongenics or near incipient isocongenics). Conversely, interbreeding of hybrids maintains knock-out viability but results in variable disease presentation. Therefore, in a preferred embodiment, two distinct isocongenic heterozygous animals are maintained by backcrossing each isocongenic heterozygous animal to its respective inbred background. Animals homozygous for the Hs3st1 gene deletion (i.e., animals carrying a null mutation in the Hs3st1 gene) are then generated by crossing the two isocongenic heterozygous animals containing the knock-out construct so that an F1 hybrid is produced. Alternatively, a similar breeding strategy may employ near incipient or incipient heterozygous isocongenics. Southern hybridization or PCR analysis of progeny DNA (e.g., tail DNA) may be conducted to identify desired genotypes.

Characteristics associated with myxomatous valvular disease in animals selected for lacking 3-OST-1 activity may be identified using well-known echocardiograph, histological or biochemical methods. For example, 3-OST-1 activity may be measured in candidate animals using the $HS^{act}$ conversion assay (e.g., Shworak, et al. (1996) supra). Further, leaflet glycosaminoglucan content (e.g., hyaluronan) may be determined. Exemplary characteristics associated with myxomatous valvular disease include, but are not limited to, focal thickening of leaflets, degradation of fibrosa collagen fibers, increased interstitial cells, accumulation of hyaluronan rich myxoid material, platelet thrombi on leaflets, left atrial thrombosis, progressive focal calcification and scerosis, reduction of valve compliance, low body weight, valvular insufficiency, cardiac arrhythmias, endocarditis, and embolic ischemia.

Animals selected for lacking 3-OST-1 activity of the present invention are useful to identify agents (e.g., small organic molecules, nucleic acids, peptides) which may be used to prevent or delay the development of or treat myxomatous valvular disease. In one embodiment, an agent that is useful for preventing or delaying the development of myxomatous valvular disease can be identified by administering a test compound or candidate agent to an animal (e.g., mouse) selected for lacking 3-OST-1 activity prior to the development (e.g., prior to ~20 to 30 weeks of age) of characteristics associated with myxomatous valvular disease. If the agent wholly or partially inhibits, delays or prevents the development of at least one of these characteristics compared to the age of development of the same characteristic in an untreated animal, then the agent is useful in preventing or delaying the development of myxomatous valvular disease.

In another embodiment, an agent that is useful for treating myxomatous valvular disease may be identified by administering a test compound or candidate agent to an animal selected for lacking 3-OST-1 activity exhibiting characteristics associated with myxomatous valvular disease. If the agent wholly or partially abates at least one of these characteristics, then the agent is useful in treating myxomatous valvular disease.

Animals of the present invention which are selected for lacking 3-OST-1 activity and exhibit characteristics associated with myxomatous valvular disease may now be made and studied and used as a model to study possible therapies including pharmaceutical intervention, gene targeting techniques, antisense therapies, antibody therapies, etc. These animals may also be used to study the progressive degeneration and the sequence of molecular events involved in this disease. Furthermore, Hs3st1 mutant in vitro cell lines may also be established and used in order to elucidate intracellular signaling systems involved in the disease as well as test and identify potentially therapeutic compounds.

Aortic banding may also be performed in animals of the present invention to induce an approximate 2-fold acceleration in the development of characteristics associated with the disease. This procedure mimics hypertension, which in humans is associated with aortic valve prolapse caused by advanced myxomatous degeneration.

Animals selected for lacking 3-OST-1 activity of the invention are also useful for the identification of previously unrecognized genes which may also play a role in this degenerative disease, either beneficial or deleterious. A transgenic animal bearing a candidate gene is crossed with an animal selected for lacking 3-OST-1 activity of the invention and the effect of the presence of the candidate gene on the myxomatous valvular disease-associated characteristics of the transgenic animal are examined.

A candidate gene will be scored as beneficial if it delays or dilutes myxomatous valvular disease-associated characteristics such as focal thickening or degradation of fibrosa collagen fibers.

Conversely, a candidate gene will be scored as favoring the development of myxomatous valvular disease if it accelerates the age of onset or severity of the disease.

The results provided herein indicate that 3-OST-1 deficiency is involved in myxomatous valvular disease in humans, providing a biological marker for the disease. Accordingly, the present invention further provides a method of diagnosing myxomatous valvular disease by detecting the level of 3-OST-1 in a sample. In one embodiment, the level of 3-OST-1 protein in a sample is detected via binding of a 3-OST-1 specific antibody in an immunoassay. In another embodiment, the level of 3-OST-1 enzyme activity is determined using, for example, the $HS^{act}$ conversion assay (Shworak, et al. (1996) supra). In another embodiment, the level of 3-OST-1 RNA transcript is determined using any number of well-known RNA-based assays for detecting levels of RNA. Once detected, the levels of 3-OST-1 are compared to a known standard. A decrease in the level of 3-OST-1, as compared to the standard, is indicative of the presence of or risk to develop myxomatous valvular disease.

For the detection of 3-OST-1 protein levels, antibodies which specifically recognize 3-OST-1 are generated. These antibodies may be either polyclonal or monoclonal. Moreover, such antibodies may be natural or partially or wholly synthetically produced. All fragments or derivatives thereof (e.g., Fab, Fab', $F(ab')_2$, scFv, Fv, or Fd fragments) which maintain the ability to specifically bind to and recognize 3-OST-1 are also included. The antibodies may be a member of any immunoglobulin class, including any of the human classes: IgG, IgM, IgA, IgD, and IgE.

The 3-OST-1 specific antibodies may be generated using classical cloning and cell fusion techniques. See, for example, Kohler and Milstein (1975) Nature 256:495–497; Harlow and Lane (1988) Antibodies: A Laboratory Manual, Cold Spring Harbor Laboratory, New York. Alternatively, antibodies which specifically bind 3-OST-1 are derived by a phage display method. Methods of producing phage display antibodies are well-known in the art (e.g., Huse, et al. (1989) Science 246(4935):1275–81).

In a preferred embodiment, 3-OST-1 specific antibodies are produced by immunizing a $Hs3st1^{-/-}$ animal with a 3-OST-1 polypeptide, or antigenic fragment thereof, to circumvent immune tolerance caused by endogenous, plasma-borne 3-OST-1.

Selection of 3-OST-1 specific antibodies is based on binding affinity and may be determined by various well-known immunoassays including, enzyme-linked immunosorbent, immunodiffusion chemiluminescent, immunofluorescent, immunohistochemical, radioimmunoassay, agglutination, complement fixation, immunoelectrophoresis, and immunoprecipitation assays and the like which may be performed in vitro, in vivo or in situ. Such standard techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) J. Clin. Chem. Clin. Biochem. 22:895–904).

Once fully characterized for specificity, the antibodies may be used in diagnostic, prognostic, or predictive methods to evaluate the levels of 3-OST-1 in healthy and diseased tissues via techniques such as ELISA, western blotting, or immunohistochemistry.

The general method for detecting levels of 3-OST-1 protein provides contacting a sample with an antibody which specifically binds 3-OST-1, washing the sample to remove non-specific interactions, and detecting the antibody-antigen complex using any one of the immunoassays described above as well a number of well-known immunoassays used to detect and/or quantitate antigens (see, for example, Harlow and Lane (1988) supra). Such well-known immunoassays include antibody capture assays, antigen capture assays, and two-antibody sandwich assays.

For the detection of nucleic acid sequences encoding 3-OST-1, either a DNA-based or RNA-based method may be employed. DNA-based methods for detecting mutations in the HS3ST1 locus (i.e., frameshift mutations, point mutations, missense mutations, nonsense mutations, splice mutations, deletions or insertions of induced, natural or inherited origin) include, but are not limited to, DNA microarray technologies, oligonucleotide hybridization (mutant and wild-type), PCR-based sequencing, single-strand conformational polymorphism (SSCP) analysis, heteroduplex analysis (HET), PCR, or denaturing gradient gel electrophoresis. Database analysis provided a human HS3ST1 gene (FIG. 2) which is structurally similar to the mouse counterpart (FIG. 1). The human HS3ST1 gene is provided as accession number NT_006342.13 with the coding region located at nucleotides 1781702–1780406. The 5' exon is located at approximately nucleotide 1810505. The coding region contains the largest concentration of targets for mutations, thus this region may be surveyed with three overlapping 450 bp PCR products (FIG. 2). Seven additional fragments (known 5' exons and 3' untranslated regions) may be screened for mutations in 5' untranslated regions regions, splice donor and acceptor sites (including the polypyrimidine tract and branch point A of the acceptor site (O'Neill, et al. (1998) *Mutat. Res.* 411:179–214)), and polyadenylation signals. Mutations may appear, for example, as a dual base call on sequencing chromatograms. Potential mutations are confirmed by multiple, independent PCR reactions. Exemplary single nucleotide polymorphisms which may be identified in accordance with the diagnostic method of the invention include, but are not limited to, NCBI SNP Cluster ID Nos. rs224486, rs224487, rs991085, rs2240901, rs224488, rs224489, rs123631, rs123630, rs3070505, rs764111, rs2109600, rs224490, rs224491, rs224492, rs224493, rs224467, rs224465, rs224466, rs224464, rs224463, rs224462, rs224461, rs224460, rs224459, rs224458, rs224457, rs224456, rs874313, rs1406076, rs1047389, rs1047385, rs1528081, rs1013274, rs1013275, rs722213 and rs722212.

To detect the levels of RNA transcript encoding the 3-OST-1, nucleic acids are isolated from cells contained in the sample, according to standard methodologies (e.g., Sambrook et al. (1989) *Molecular Cloning, a Laboratory Manual*, Cold Spring Harbor Laboratories, New York). The nucleic acid may be whole cell RNA or fractionated to Poly-A+. It may be desired to convert the RNA to a complementary DNA (cDNA). Normally, the nucleic acid is amplified.

A variety of methods may be used to evaluate or quantitate the level of 3-OST-1 RNA transcript present in the nucleic acids isolated from a sample. For example, levels of 3-OST-1 RNA transcript may be evaluated using well-known methods such as northern blot analysis (see, e.g., Sambrook et al. (1989) *Molecular Cloning, a Laboratory Manual*, Cold Spring Harbor Laboratories, New York); oligonucleotide or cDNA fragment hybridization wherein the oligonucleotide or cDNA is configured in an array on a chip or wafer; real-time PCR analysis, or RT-PCR analysis.

Suitable primers, probes, or oligonucleotides useful for such detection methods may be generated by the skilled artisan from the nucleic acid sequence encoding 3-OST-1 (GENBANK accession number AF019386). The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred. Probes are defined differently, although they may act as primers. Probes, while perhaps capable of priming, are designed for binding to the target DNA or RNA and need not be used in an amplification process. In a preferred embodiment, the probes or primers are labeled with, for example, radioactive species ($^{32}P$, $^{14}C$, $^{35}S$, $^{3}H$, or other label) or a fluorophore (rhodamine, fluorescein). Depending on the application, the probes or primers may be used cold, i.e., unlabeled, and the RNA or cDNA molecules are labeled.

Various RT-PCR methodologies may be employed to evaluate the level of 3-OST-1 RNA transcript present in a sample. As clinical samples are of variable quantity and quality a relative quantitative RT-PCR reaction may be performed with an internal standard. The internal standard may be an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other assays may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

Depending on the format, detection may be performed by visual means (e.g., ethidium bromide staining of a gel). Alternatively, the detection may involve indirect identification of the product via chemiluminescence, radiolabel or fluorescent label or even via a system using electrical or thermal impulse signals (Bellus (1994) *J. Macromol. Sci. Pure Appl. Chem.* A311:1355–1376).

After detecting the levels of 3-OST-1 present in a sample, said levels are compared with a known standard. A known standard may be a statistically significant reference group of normal individuals and individuals that have myxomatous valvular disease to provide diagnostic, prognostic, or predictive information pertaining to the individual from whom the sample was obtained.

It is contemplated that the diagnostic method is useful for detecting myxomatous valvular disease in humans as well as other animals such as dogs.

The present invention also provides a kit which is useful for carrying out the present invention. The present kit comprises a container containing an antibody which specifically binds 3-OST-1. The kit also comprises other solutions necessary or convenient for carrying out the invention. The container can be made of glass, plastic or foil and can be a vial, bottle, pouch, tube, bag, etc. The kit may also contain written information, such as procedures for carrying out the present invention or analytical information, such as the amount of reagent contained in the first container. The container may be in another container, e.g., a box or a bag, along with the written information.

EXAMPLE 1

Generation of Hs3st1$^{-/-}$ Mice

The Hs3st1 coding region was isolated by PCR screening an arrayed P1 library of 129P2/OlaHsd genomic DNA (Incyte Genomics, St. Louis, Mo.) with two different oligonucleotide sets designed to amplify 5' and 3' untranslated region sequences of Hs3st1. Primers 5'-dATTGGCAACTG-GAGATACTCATGT (SEQ ID NO:1) and 5'-dTGCCT-TCTCCGGTGTCCTCT (SEQ ID NO:2) amplify nucleotides 219–467; whereas, 5'-dTTCTGTACAGTATTAGAT TCA CAGT (SEQ ID NO:3) with 5'-dGCTATTTTGGAT-TGGAGGCAGGT (SEQ ID NO:4) amplify nucleotides 1383–1617 from the mouse Hs3st1 cDNA sequence (Shworak, et al. (1997) supra). Three independent overlapping genomic clones were recovered, exons were mapped by Southern blot analysis and the coding region was verified by DNA sequence analysis to reveal that exon 8 contained the entire coding region.

A targeting construct was generated from pMCIDT-A which contains an expression cassette for diphtheria toxin A (DTA) for positive selection. The targeting construct was designed to replace a 2.5 kb genomic region, (SpeI/BglI) encompassing the Hs3st1 coding region, with a 1.8 kb (XhoI/BamHI) neo$^r$ expression cassette from pPNT (Tybulewicz, et al. (1991) *Cell* 65:1153–1163). The 5' targeting sequence was a 2.3 kb SphI/SpeI fragment and the 3' region was a 4.8 kb BglI/SphI fragment. Targeted D3 embryonic stem (ES) cells were generated and injected into C57BL/6 blastocysts using well-known methods (Enjyoji, et al. (1999) *Nat. Med.* 5:1010–1017).

Initially, genotyping was conducted by Southern blot analysis. BamHI-digested genomic DNA from ES cell clones or mouse tails was hybridized to external probes generated by PCR of cloned genomic sequences. A 120 bp 5' probe was obtained with 5'-dGGATCCCTCGCCTG-GTCTTAC (SEQ ID NO:5) and 5'-dTCTAGAAGT-CAAATATACACAGAGT (SEQ ID NO:6); whereas, a 521 bp 3' probe was amplified with 5'-dCTCCTGAGTCAC-CTACACTGAG (SEQ ID NO:7) and 5'-dGGATCCAG-GACTAACTGACTTTT (SEQ ID NO:8). Subsequently, genotyping was conducted by heteroduplex PCR. The wild-type allele generates a 235 bp fragment with 5'-dTTCTG-TACAGTATTAGATTCACAGT (SEQ ID NO:9) and 5'-dGCTATTTTGGATTGGAGGCAGGT (SEQ ID NO:10); whereas, the knock-out allele produces a 380 bp product with 5'-dGCCAGCGGGGCTGCTAAA (SEQ ID NO:11) and 5'-dGCAGAGATGAGTTCCGCTTAC (SEQ ID NO:12).

Chimeras were bred to C57BL/6 mice (The Jackson Laboratory, Bar Harbor, Me.) and heterozygous progeny were interbred to create F2 individuals of ~50/50 mixed genetic background, which were used for all characterizations unless indicated otherwise. Chimeras were also bred to the well-known 129S4/SvJae mouse strain to place the knock-out allele on an incipient congenic background. The Hs3st1$^{+/-}$ 129S4/SvJae mice were maintained through backcrossing as the Hs3st1$^{-/-}$ genotype exhibited partial lethality (~40%) in this strain.

Noon on the day of vaginal plug appearance was defined as 0.5 gestational days (E0.5). Females were sacrificed on E18.5 and embryos were isolated with placentae attached. Neonates were harvested on the day of or one day after birth. Tail tissue, ~3 mm, was harvested for genotyping. Perinatals were incubated in Bouin's solution for 48 hours then washed in several changes of 70% ethanol over 3 weeks. Placentae were removed and disks comprised solely of labyrinth and spongiotrophoblast layers were isolated from umbilical cords and membranes and then weighed. Fixation reduced embryo mass by ~14%, irrespective of genotype. Biparietal diameter was measured with a digital caliper. Perinatal anatomy was assessed from crown to rump serial cross sections taken every 100–300 µm.

EXAMPLE 2

Characterization of 3-OST-1 Deficient Mice

All experimental animals were generated from Hs3st1$^{+/-}$× Hs3st1$^{+/-}$ crosses. Experimental groupings employed age and sex matched littermates. Unless otherwise indicated, all data are expressed as the mean±S.E.M. and statistical significance was evaluated by two-tailed Student's t-test.

For analysis of T•AT complexes, immediately after arterial injury a 0.5 cc syringe containing 30 µl of 3.8% trisodium citrate was used to draw ~300 up blood by a single puncture of the left ventricle. Otherwise ~170 µl of blood was collected, during tail tissue collection, in tubes containing 10 µl of 3.8% trisodium citrate. Plasma was prepared by two sequential centrifugations then frozen on liquid N2 and stored at −80° C. For determination of 3-OST-1 activity, 70 µl of fresh plasma was combined with 0.91 µl of 77 µg/ml pepstatin, 770 µg/ml leupeptin, 150 µg/ml aprotinin (Sigma, St. Louis, Mo.), and 77 mM PEFABLOC® SC (Boehringer Mannheim, Mannheim, GER) then frozen.

For the isolation of tissue homogenates and tissue heparan sulfate (HS), mice were anesthetized with avertin, then PBS was perfused into the left ventricle and blood was drained from the right jugular vein until clear. Organs were weighed, frozen in liquid nitrogen then ground with a polytron at 25,000 rpm for 3 minutes in 2 ml of ice chilled 25 mM MES, pH 6.5, 250 mM sucrose, 1% TRITON® with 26 µl of the protease inhibitor mix provided herein. For tissue homogenates, a 0.3 ml portion was centrifuged at 10,000×g for 1 hour at 4° C., 200 µl of clear supernatant was collected, protein concentration was determined by Bradford (Bradford (1976) *Anal. Biochem.* 72:248–254) with bovine serum albumin as standard, then homogenates were frozen on liquid nitrogen and stored at −80° C. The remaining ~1.6 ml of extract was sonicated five times, 3 seconds each pulse, then 10$^6$ cpm of tracer [$^{35}$S]HS was added to correct for extraction losses. Glycosaminoglycans were cleaved from proteoglycans by addition of 36 µl of 5.6 M NaOH with 4.4 M sodium borohydride and refluxing at 46° C. for 12 hours. After centrifugation at 10,000×g for 20 minutes, ice-chilled supernatants were slowly added to 0.5 ml of 8.54 M ammonium formate containing 1.7 M HCl and vortexed in a 15 ml tube. After centrifugation at 10,000×g, supernatants were extracted four times against 5 ml of phenol, thrice against 7 ml of phenol:chloroform:isoamyl alcohol (25:24:1), and once each against 3 ml of chloroform:isoamyl alcohol (24:1) and 6 ml isobutanol. Glycosaminoglycans were precipitated with 5 ml ethanol then harvested by centrifugation at 10,000×g for 1.5 hours. Pellets were resuspended in 100 µl water and chondroitin sulfate was degraded with 0.02 Units of chondroitinase ABC (Shworak, et al. (1996) supra). HS was purified by phenol extraction and ethanol precipitation (Shworak, et al. (1996) supra), then mass was determined by forming complexes with alcian blue (Fluka, Buchs, Switzerland) (Björnsson (1998) *Anal. Biochem.* 256:229–237)

using kidney HS (ICN Pharmaceuticals, Inc., Costa Mesa, Calif.) as standard. Complexes were harvested by centrifugation at 10,000×g for 30 minutes then resuspended in 100 µl of 8 M guanidine HCl with 0.1% TRITON® X-100 and spectrophotometrically measured at $A_{600}$.

The $HS^{act}$ conversion assay (Shworak, et al. (1996) supra) measures 3-OST-1 formation of AT-binding sites. In the presence of 3'-phosphoadenosine 5'-phosphosulfate (PAPS), 3-OST-1 converts [$^{35}$S]HS, lacking 3-O-sulfates, into [$^{35}$S] $HS^{act}$, which contains AT-binding sites and is quantified by AT-affinity chromatography (Shworak, et al. (1994) supra). [$^{35}$S]HS lacking 3-O-sulfates was prepared from metabolically labeled CHO-KI cells, and reactions containing 80,000 cpm of [$^{35}$S]HS were assembled using a well-known method (Yabe, et al. (2001) supra) with the following modifications to optimize sensitivity. Plasma (1 µl) or lung homogenates (20 µg) were analyzed in reactions containing 0.4 mg/ml chondroitin sulfate C and lacking NaCl and glycogen. Reactions for brain (10 µg) or heart (40 µg) homogenates lacked chondroitin sulfate, NaCl and glycogen. Activity was calibrated against purified recombinant 3-OST-1 standards, which were run in the absence and presence of plasma and tissue homogenates.

The in vitro activity of tissue HS to enhance AT neutralization of factor Xa was determined as previously described using S-2765 to monitor Xa activity (Marcum and Rosenberg (1985) *Biochem. Biophys. Res. Commun.* 126:365–372). Activity was calibrated against a standard curve of porcine heparin (Sigma H-3393, 179 USP U/mg, Sigma, St. Louis, Mo.). HCII activity was similarly detected using 205 nM human HCII with 125 nM human α-thrombin (Haemotologic Technologies, Inc.) and substrate S-2238 (DiaPharma Group, West Chester, Ohio). Plasma AT activity (anti-Xa activity) was measured with a COAMATIC® Antithrombin (Chromogenix, Milano, Italy) kit according to the manufacturer's specifications and using purified AT (Cutter Laboratories, Berkeley, Calif.) as standard. Plasma T•AT level was measured with an enzyme immunoassay using the ENZYGNOST® TAT micro (Dade Behring, Deerfield, Ill.) kit.

For determination of tissue AT-binding, organs (10 mg portions) were extracted twice in 500 ml of 50 mM Tris-HCl buffer, pH 8.0, containing 8 M urea, 10 mM EDTA, 1 mM PMSF and 1 M DTT, in a Potter homogenizer at room temperature. The pooled extracts were clarified by centrifugation for 30 minutes at 10,000×g and the supernatants were filtered through a 0.22 mm MILLEX®-GV filter. The protein concentration of tissue extracts was determined using the bicinchoninic acid reagent (Pierce, Rockford, Ill.). Aliquots of the tissue extracts containing 2 to 20 mg proteins were loaded in triplicate onto nitrocellulose membrane using a dot-blot apparatus and $^{125}$I-AT ligand-binding assay was performed using a standard method (de Agostini, et al. (1994) *J. Cell. Biochem.* 54:174–185).

For in situ detection of AT-binding sites, tissue isolation, generation of cryosections, incubation of sections with $^{125}$I-labeled AT, and autoradiography were all performed using standard methods (Princivalle, et al. (2001) *Glycobiology* 11:183–194). Specificity of AT binding to $HS^{act}$ was confirmed by competition with soluble sulfated polysaccharides and by preincubation with GAG lyases (Princivalle, et al. (2001) supra).

To determine tissue fibrin levels, urea insoluble tissue extracts (containing cross-linked fibrin) were prepared and fibrin was measured by western blot analysis with a fibrin specific antibody, NYB T2G1 (Christie, et al. (1999) *J. Clin. Invest.* 104:533–539). Subsets of mice were subjected to overnight hypoxia (8% $O_2$) to induce procoagulant changes in lung tissue (Weiler-Guettler, et al. (1998) *J. Clin. Invest.* 101:1983–1991).

To measure acute carotid artery injury, $FeCl_3$-induced arterial injury was performed similar to published procedures (Weiler, et al. (2001) *Arterioscler. Thromb. Vasc. Biol.* 21:1531–1537). Analyses of inbred mouse lines showed that injury responses were very different for C57BL/6 vs. 129S4/SvJae strains and that F2 hybrids yielded mice with extremely variable responses. Given this dependency on genetic background, studies were only conducted with incipient congenic 129S4/SvJae mice. Mice (25–35 grams) were anesthetized with 1.25% avertin (0.34 mg/g intraperitoneally), intubated and ventilated (14 ml/g; 111 breaths/minute). The right and left common carotid arteries were exposed by blunt dissection. Miniature Doppler flow probes (model 0.5VB, Transonic Systems, Ithaca, N.Y.) were positioned around the distal limit of each common carotid artery and blood flow in both arteries was recorded simultaneously. Ten minutes after probe placement, the left carotid artery was chemically injured by applying a 1.0×0.6 mm strip of filter paper soaked in 30% $FeCl_3$ to the proximal adventitial surface for 1 minute. The field was flushed with saline and flow was monitored until complete occlusion occurred. The injury procedure was then repeated on the right common carotid. Flow was measured with a Transonic T206 meter using a 30 Hz filter and data was acquired with WinDaq software (DATAQ® Instruments, Akron, Ohio). Fast Fourier transformation identified the point at which flow was undetectable. Occlusion times were not correlated to initial blood flow rates (Hs3st1$^{+/+}$ $r^2$<0.001; Hs3st1$^{-/-}$ $r^2$=0.0314) so data were not adjusted for initial flow. Injured arteries were collected in Bouin's fixative and platelet rich thrombi were confirmed with hematoxylin and eosin staining of paraffin sections. 3-OST-1.

What is claimed is:

1. A method of producing a mouse model of myxomatous valvular disease comprising the steps of:

a) introducing a transgene containing 3-O-sulfotransferase-1 nucleic acid sequences that flank a selectable marker gene into a mouse embryonic stem cell, wherein the transgene integrates into the genome of the mouse embryonic stem cell and the selectable marker gene disrupts the endogenous 3-O-sulfotransferase-1 gene, thereby producing a mouse embryonic stem cell wherein the endogenous 3-O-sulfotransferase-1 gene has been disrupted;

b) introducing the mouse embryonic stem cell wherein the endogenous 3-O-sulfotransferase-1 gene has been disrupted, into a mouse embryo;

c) implanting the resulting mouse embryo comprising the mouse ES cell of (b), into the uterus of a pseudopregnant mouse, wherein the pseudopregnant mouse gives birth to a chimeric mouse;

d) breeding the chimeric mouse to produce a mouse heterozygous for a disruption in the 3-O-sulfotransferase-1 gene;

e) backcrossing the heterozygous mouse for at least 10 backcrosses to produce a mouse that is heterozygous for the disrupted 3-O-sulfotransferase1 gene; and f) crossing a first mouse obtained in step (e) with a second mouse obtained in step (e) to produce a homozygous knock-out mouse lacking heparan sulfate 3-O-sulfotransferase-1 activity and exhibiting mitral valve degeneration, indicative of myxomatous valvular disease.

2. A method of screening an agent for the treatment of myxomatous valvular disease comprising administering an agent to a homozygous knock-out mouse produced by step (f) of the method of claim 1, and determining whether the agent at least partially abates at least one of the characteristics of myxomatous valvular disease in said mouse.

3. A method of screening for an agent that prevents or delays the development of myxomatous valvular disease comprising administering an agent to a homozygous knock-out mouse produced by step (f) of the method of claim 1 and determining whether the agent at least partially prevents or delays the age of development of at least one of the characteristics of myxomatous valvular disease in said mouse compared to the age development of said characteristic in an untreated mouse.

4. A mouse model of myxomatous valvular disease produced by step (f) of the method of claim 1, wherein the mouse lacks heparan sulfate 3-O-sulfotransferase-1 activity and exhibits mitral valve degeneration, indicative of myxomatous valvular disease.

* * * * *

UNITED STATES PATENT AND TRADEMARK OFFICE
CERTIFICATE OF CORRECTION

PATENT NO. : 7,166,763 B2
APPLICATION NO. : 10/365140
DATED : January 23, 2007
INVENTOR(S) : Nicholas W. Shworak et al.

Page 1 of 1

It is certified that error appears in the above-identified patent and that said Letters Patent is hereby corrected as shown below:

At column 1, line 6, please delete

"This invention was made in the course of research sponsored by the National Institutes of Health (NIH Grant No. PO1 HL41484-12). The U.S. government may have certain rights in this Invention."

At column 1, line 6, please insert

--This invention was made with Government support under Grant No. PO1 HL066105 awarded by the National Institutes of Health. The Government has certain rights in this invention.--

Signed and Sealed this
Tenth Day of May, 2011

David J. Kappos
*Director of the United States Patent and Trademark Office*